United States Patent
Barry

(10) Patent No.: US 10,765,460 B2
(45) Date of Patent: *Sep. 8, 2020

(54) SYSTEM AND METHOD FOR ALIGNING VERTEBRAE IN THE AMELIORATION OF ABERRANT SPINAL COLUMN DEVIATION CONDITIONS

(71) Applicant: Mark A. Barry, Las Vegas, NV (US)

(72) Inventor: Mark A. Barry, Las Vegas, NV (US)

(73) Assignee: Mark A. Barry, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/615,515

(22) Filed: Jun. 6, 2017

(65) Prior Publication Data

US 2017/0273723 A1    Sep. 28, 2017

Related U.S. Application Data

(60) Continuation of application No. 15/249,261, filed on Aug. 26, 2016, now Pat. No. 9,668,788, which is a
(Continued)

(51) Int. Cl.
*A61B 17/70* (2006.01)
*A61B 17/56* (2006.01)
*A61B 17/68* (2006.01)

(52) U.S. Cl.
CPC ...... *A61B 17/7079* (2013.01); *A61B 17/7002* (2013.01); *A61B 17/708* (2013.01);
(Continued)

(58) Field of Classification Search
CPC ............ A61B 17/7079; A61B 17/7049; A61B 17/708; A61B 17/7032; A61B 17/7077; A61B 17/7076; A61B 2017/681

See application file for complete search history.

(56) References Cited

U.S. PATENT DOCUMENTS 5,102,412 A   4/1992   Rogozinski
5,112,332 A   5/1992   Cozad et al.
(Continued)

FOREIGN PATENT DOCUMENTS

DE   10125717 A   12/2002
EP   0553782 B1   1/1993
(Continued)

OTHER PUBLICATIONS

Schlenk et al.; Biomechanics of spinal deformity; Neurosurg. Focus; 14 (1) e2; pp. 1-15; Jan. 2003.
(Continued)

*Primary Examiner* — Ellen C Hammond

(74) *Attorney, Agent, or Firm* — Shay Glenn LLP

(57) ABSTRACT

A system for applying a manipulative force to a target region of a spinal column during a surgical procedure is provided with at least four pedicle screws, at least four elongated levers configured to temporarily engage with the pedicle screws, a linking member configured to link at least two of the elongated levers in a axial direction such that they move in unison, and a cross-linking member configured to link at least two of the elongated levers in a transverse direction such that they move in unison. When the system is assembled, it permits an operator to move the at least four elongated levers in unison to simultaneously rotate the at least four pedicle screws about a spinal column roll axis. Related methods are also provided.

30 Claims, 5 Drawing Sheets

Related U.S. Application Data division of application No. 15/154,703, filed on May 13, 2016, now Pat. No. 9,668,787, which is a continuation of application No. 13/645,589, filed on Oct. 5, 2012, now Pat. No. 9,339,301, which is a continuation of application No. 12/857,320, filed on Aug. 16, 2010, now Pat. No. 8,361,121, which is a continuation of application No. 11/202,409, filed on Aug. 10, 2005, now Pat. No. 7,776,072, which is a continuation-in-part of application No. 11/027,026, filed on Dec. 30, 2004, now Pat. No. 7,670,358.

(52) U.S. Cl.
CPC ...... *A61B 17/7032* (2013.01); *A61B 17/7049* (2013.01); *A61B 17/7077* (2013.01); *A61B 17/7076* (2013.01); *A61B 2017/564* (2013.01); *A61B 2017/567* (2013.01); *A61B 2017/681* (2013.01)

(56) References Cited

U.S. PATENT DOCUMENTS

| | | | |
|---|---|---|---|
| 5,116,334 | A | 5/1992 | Cozad et al. |
| 5,281,223 | A | 1/1994 | Ray |
| 5,282,863 | A | 2/1994 | Burton |
| 5,306,275 | A | 4/1994 | Bryan |
| 5,466,238 | A | 11/1995 | Lin |
| 5,498,262 | A | 3/1996 | Bryan |
| 5,545,166 | A | 8/1996 | Howland |
| 5,591,235 | A | 1/1997 | Kuslich |
| 5,630,816 | A | 5/1997 | Kambin |
| 5,676,665 | A | 10/1997 | Bryan |
| 5,704,937 | A | 1/1998 | Martin |
| 5,707,372 | A | 1/1998 | Errico et al. |
| 5,772,661 | A | 6/1998 | Michelson |
| 5,797,910 | A | 8/1998 | Martin |
| 5,810,817 | A * | 9/1998 | Roussouly ......... A61B 17/7041 606/250 |
| 5,928,232 | A | 7/1999 | Howland et al. |
| 5,947,965 | A | 9/1999 | Bryan |
| 6,015,409 | A | 1/2000 | Jackson |
| 6,083,226 | A | 7/2000 | Fiz |
| 6,090,113 | A * | 7/2000 | Le Couedic ......... A61B 17/708 606/86 A |
| 6,113,600 | A | 9/2000 | Drummond et al. |
| 6,217,578 | B1 | 4/2001 | Crozet et al. |
| 6,235,028 | B1 * | 5/2001 | Brumfield ......... A61B 17/7083 606/53 |
| 6,267,765 | B1 | 7/2001 | Taylor et al. |
| 6,375,657 | B1 | 4/2002 | Doubler et al. |
| 6,440,132 | B1 | 8/2002 | Jackson |
| 6,458,131 | B1 | 10/2002 | Ray |
| 6,558,390 | B2 | 5/2003 | Cragg |
| 6,645,207 | B2 | 11/2003 | Dixon et al. |
| 6,652,526 | B1 | 11/2003 | Arafiles |
| 6,743,231 | B1 | 6/2004 | Gray et al. |
| 6,749,614 | B2 | 6/2004 | Teitelbaum et al. |
| 6,755,828 | B2 * | 6/2004 | Shevtsov ......... A61B 17/7043 606/246 |
| 6,783,526 | B1 | 8/2004 | Lin et al. |
| 6,802,844 | B2 | 10/2004 | Ferree |
| 6,821,277 | B2 | 11/2004 | Teitelbaum |
| 6,827,719 | B2 | 12/2004 | Ralph et al. |
| 6,884,241 | B2 | 4/2005 | Bertranou et al. |
| 7,011,658 | B2 | 3/2006 | Young |
| 7,188,626 | B2 | 3/2007 | Foley et al. |
| 7,507,248 | B2 | 3/2009 | Beaurain et al. |
| 7,670,358 | B2 | 3/2010 | Barry |
| 7,776,072 | B2 | 8/2010 | Barry |
| 7,828,825 | B2 | 11/2010 | Bruneau et al. |
| 7,927,357 | B2 | 4/2011 | Sacher et al. |
| 7,931,675 | B2 | 4/2011 | Panjabi et al. |
| 7,951,175 | B2 | 5/2011 | Chao et al. |
| 8,025,679 | B2 | 9/2011 | Nichcls et al. |
| 8,147,524 | B2 | 4/2012 | Piza Vallespir |
| 8,361,121 | B2 | 1/2013 | Barry |
| 9,339,301 | B2 | 5/2016 | Barry |
| 9,668,787 | B2 | 6/2017 | Barry |
| 9,668,788 | B2 | 6/2017 | Barry |
| 2002/0116001 | A1 | 8/2002 | Schafer et al. |
| 2003/0065328 | A1 * | 4/2003 | Shevtsov ......... A61B 17/7043 606/54 |
| 2005/0033291 | A1 * | 2/2005 | Ebara ......... A61B 17/7034 606/53 |
| 2005/0085812 | A1 | 4/2005 | Sherman et al. |
| 2005/0203516 | A1 | 9/2005 | Biedermann et al. |
| 2005/0203518 | A1 | 9/2005 | Biedermann et al. |
| 2005/0203519 | A1 | 9/2005 | Harms et al. |
| 2005/0228377 | A1 | 10/2005 | Chao et al. |
| 2005/0245928 | A1 | 11/2005 | Colleran et al. |
| 2005/0273099 | A1 | 12/2005 | Baccelli et al. |
| 2005/0277922 | A1 | 12/2005 | Trieu et al. |
| 2006/0009767 | A1 | 1/2006 | Kiester |
| 2006/0025768 | A1 | 2/2006 | Iott et al. |
| 2006/0036240 | A1 | 2/2006 | Colleran et al. |
| 2006/0047282 | A1 | 3/2006 | Gordon |
| 2006/0173454 | A1 | 8/2006 | Spitler et al. |
| 2006/0195088 | A1 | 8/2006 | Sacher et al. |
| 2006/0195093 | A1 | 8/2006 | Jahng |
| 2006/0200130 | A1 | 9/2006 | Hawkins et al. |
| 2006/0241594 | A1 | 10/2006 | McCarthy et al. |
| 2006/0264935 | A1 | 11/2006 | White |
| 2006/0264937 | A1 | 11/2006 | White |
| 2010/0106192 | A1 | 4/2010 | Barry |
| 2010/0106193 | A1 | 4/2010 | Barry |
| 2010/0249844 | A1 | 9/2010 | Durrani |
| 2012/0271353 | A1 | 10/2012 | Barry |

FOREIGN PATENT DOCUMENTS

| | | |
|---|---|---|
| WO | WO94110944 A1 | 5/1994 |
| WO | WO2005/089656 A1 | 9/2005 |
| WO | WO2005/089657 A1 | 9/2005 |
| WO | WO2005/092218 A1 | 10/2005 |

OTHER PUBLICATIONS

Medtronic's Letter Brief requesting summary judement of invalidity under 35 U.S.C. 102(b), and associated Exhibits, in *Mark A. Barry, MD* v. *Medtronic, Inc.*, Civil Action No. 1:14-cv-00104-RC, filed with the United States District Court for the Eastern District of Texas on Jun. 3, 2015.

Dr. Barry's Response to Medtronic's Letter Brief requesting summary judment, and associated Exhibits, in *Mark A. Barry, MD* v. *Medtronic, Inc.*, Civil Action No. 1:14-cv-00104-RC, filed with the United States District Court for the Eastern District of Texas on Jun. 17, 2015.

Medtronic's Motion to Disqualify, and associated Exhibits A-1, in *Mark A. Barry, MD* v. *Medtronic, Inc.*, Civil Action No. 1:14-cv-00104-RC, filed with the United States District Court for the Eastern District of Texas on Jun. 25, 2015.

Dr. Barry's Notice of Sur-Reply to Defendant's Reply, and associated Exhibits, in *Mark A. Barry, MD* v. *Medtronic, Inc.*, Civil Action No. 1:14-cv-00104-RC, filed with the United States District Court for the Eastern District of Texas on Jul. 10, 2015.

Dr. Barry's Response in Opposition to Motion to Disqualify, and associated Exhibits A-U, in *Mark A. Barry, MD* v. *Medtronic, Inc.*, Civil Action No. 1:14-cv-00104-RC, filed with the United States District Court for the Eastern District of Texas on Jul. 10, 2015.

Medtronic's First Amended Answer, Defenses and Counterclaims, in *Mark A. Barry, MD* v. *Medtronic, Inc.*, Civil Action No. 1:14-cv-00104-RC, filed with the United States District Court for the Eastern District of Texas on Jul. 20, 2015.

Medtronic's Reply Memorandum of Law in Further Support of its Motion to Disqualify, in *Mark A. Barry, MD* v. *Medtronic, Inc.*, Civil Action No. 1:14-cv-00104-RC, filed with the United States District Court for the Eastern District of Texas on Jul. 20, 2015.

(56) References Cited

OTHER PUBLICATIONS

Order on Motion to Withdraw and Substitute Lead Counsel and Motion to Disqualify the Law Firm, in *Mark A. Barry, MD* v. *Medtronic, Inc.*, Civil Action No. 1:14-cv-00104-RC, filed with the United States District Court for the Eastern District of Texas on Aug. 14, 2015.

*Medtronic, Inc.* v. *Mark A. Barry*; Final Written Decision (Paper No. 51); Case IPR2015-00780; U.S. Pat. No. 7,670,358; 40 pages; Sep. 7, 2016.

*Medtronic, Inc.* v. *Mark A. Barry*; Final Written Decision (Paper No. 51); Case IPR2015-00783; U.S. Pat. No. 7,776,072; 47 pages; Sep. 7, 2016.

*Medtronic Inc.* v. *Mark A. Barry*; Denial of Patent Owner's Motion for Certificate of Correction (Paper 50); Case IPR2015-00780; U.S. Pat. No. 7,670,358; 9 pages; Sep. 7, 2016.

*Medtronic Inc.* v. *Mark A. Barry*; Denial of Patent Owner's Motion for Certificate of Correction (Paper 50); Case IPR2015-00783; U.S. Pat. No. 7,776,072; 9 pages; Sep. 7, 2016.

Lenke et al.; Advanced concepts in spinal deformity surgery; Medtronic Safomar Danek; May 2003.

Rinella et al.; Posterior and spinal instrumentation techniques for spinal deformity. Master Techniques in Orthopaedic Surgery; pp. 231-246; 2004.

Lee et al.; Direct vertebral rotation: A new technique of three-dimensional deformity correction with segmental pedicle screw fixation in adolescent idiopathic scoliosis; Spine Journal; 29 (3); pp. 343-349; Feb. 1, 2004.

\* cited by examiner

SYSTEM AND METHOD FOR ALIGNING VERTEBRAE IN THE AMELIORATION OF ABERRANT SPINAL COLUMN DEVIATION CONDITIONS

CROSS REFERENCE TO RELATED APPLICATIONS

This application is a continuation of U.S. application Ser. No. 15/249,261, filed Aug. 26, 2016, which is a divisional of U.S. application Ser. No. 15/154,703, filed May 13, 2016, now U.S. Pat. No. 9,668,787, which is a continuation of U.S. application Ser. No. 13/645,589, filed Oct. 5, 2012, now U.S. Pat. No. 9,339,301, which is a continuation of U.S. application Ser. No. 12/857,320, filed Aug. 16, 2010, now U.S. Pat. No. 8,361,121, which is a continuation of U.S. application Ser. No. 11/202,409, filed Aug. 10, 2005, now U.S. Pat. No. 7,776,072, which is a continuation-in-part of U.S. application Ser. No. 11/027,026, filed Dec. 30, 2004, now U.S. Pat. No. 7,670,358. These applications are herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present invention relates to methods and apparatus for management and correction of spinal deformities, such as scoliosis.

BACKGROUND

A serious deficiency presently exists with respect to conventional treatment and instrumentation for treating spinal deviation anomalies, such as scoliosis.

This circumstance presents a serious medical challenge, because scoliosis, other than mild to moderate cases, is a well-recognized health risk.

If scoliosis curvature exceeds 70 degrees, severe twisting of the spine occurs. This can cause the ribs to press against the lungs, restrict breathing, and reduce oxygen levels. The distortions may also affect the heart and possibly cause dangerous changes.

Eventually, if the curve reaches more than 100 degrees, both the lungs and the heart can be injured. Patients with this degree of severity are susceptible to lung infections and pneumonia. Curves greater than 100 degrees are associated with elevated mortality rates. A number of factors associated with scoliosis increase the risk for bone loss, which is referred to as osteopenia. People with osteopenia are at greatly increased risk of osteoporosis, a common problem in older women that can cause broken bones and is particularly dangerous for women with a history of scoliosis. Experts recommend that children with scoliosis be screened for osteopenia so that measures can be taken to help prevent osteoporosis later.

Present treatment regimens for scoliosis carry their own risks and side effects, which include:

Spinal fusion disease. Patients who are surgically treated with fusion techniques lose flexibility and may experience weakness in back muscles due to injuries during surgery.

Disk degeneration and low back pain. With disk degeneration, the disks between the vertebrae may become weakened and may rupture.

Height loss.

Lumbar flatback. This condition is most often the result of a scoliosis surgical procedure called the Harrington technique, used to eliminate lordosis (exaggeration of the inward curve in the lower back). Adult patients with flatback syndrome tend to stoop forward. They may experience fatigue and back pain and even neck pain.

Rotational trunk shift (uneven shoulders and hips).

In some patients, years after the original surgery (particularly with the first generation of Harrington rods), the weight of the instrumentation can cause disk and joint degeneration severe enough to require surgery. Treatment may involve removal of the old instrumentation and extension of the fusion into the lower back.

Left untreated, or ineffectively treated, scoliosis carries long-term consequences.

Pain in adult-onset or untreated childhood scoliosis often develops because of posture problems that cause uneven stresses on the back, hips, shoulders, necks, and legs. Studies report, however, that patients with childhood scoliosis have the same incidence of back pain as the general population, which is very high (60% to 80%). In one study conducted 20 years after growth had stopped two-thirds of adults who had lived with curvatures of 20 to 55 degrees reported back pain. In this study, most cases were mild, although other studies have reported that adults with a history of scoliosis tend to have chronic and more back pain than the general population.

Nearly all individuals with untreated scoliosis at some point develop spondylosis, an arthritic condition in the spine. The joints become inflamed, the cartilage that cushions the disks may thin, and bone spurs may develop. If the disk degenerates or the curvature progresses to the point that the spinal vertebrae begin pressing on the nerves, pain can be very severe and may require surgery. Even surgically treated patients are at risk for spondylosis if inflammation occurs in vertebrae around the fusion site.

The consequences of scoliosis are limited to the physical realm. The emotional impact of scoliosis, particularly on young girls or boys during their most vulnerable years, should not be underestimated. Adults who have had scoliosis and its treatments often recall significant social isolation and physical pain. Follow-up studies of children with scoliosis who did not have strong family and professional support often report significant behavioral problems.

Older people with a history of scoliosis, even those whose conditions were corrected, should realize that some negative emotional events in adulthood may possibly have their roots in their early experiences with scoliosis. Many studies have reported that patients who were treated for scoliosis have limited social activities and a poorer body image in adulthood. Some patients with a history of scoliosis have reported a slight negative effect on their sexual life. Pain appears to be only a minor reason for such limitation. An early Scandinavian study reported that adults with scoliosis had fewer job opportunities and a lower marriage rate than the general population.

It is clear, then, that scoliosis treatment options are presently lacking, and untreated scoliosis (except for mild to lower-moderate cases) is not an acceptable alternative. There are many apparatus which are designed for attachment to, and positioning adjacent the spinal column, and in many instances, these apparatus are designed for use in treating spinal column anomalies, such as scoliosis. However, all known systems are limited by their design and known implementation modes on either arresting further deleterious rotation of the involved vertebrae, or fixing individual vertebrae once, by some means, they are brought to approximate a desired orientation and position.

Significant correction of severe scoliotic curvature to the point of approximating normal spinal configuration, particularly by a single process, is simply unknown in the art. This is, it is believed, the result of focus in the field on the positioning substantially seriatim of affected vertebrae. Applying derotational force to a vertebrae in this manner cannot effect en mass spinal reconfiguration without risking vertebral fracture at the point of spinal instrumentation fixation, particularly when using conventional instrumentation. Furthermore, significant, focused force applied to any individual vertebra risks spinal cord and related injury. Thus, only force which is inadequate to effect substantial correction to the entire spinal column is thus far ever applied, and correction of scoliotic curvatures are substantially limited.

It has become clear to the present inventor that desired levels of correction of spinal column anomalies, such as scoliosis, can only be achieved if the spinal column (or an affected segment thereof) is manipulated (or "derotated") substantially as a whole into a desired configuration. To achieve such an objective, force must be applied safely to all to-be-derotated vertebrae, and the forces necessary to reconfigure all, or at least a substantial portion of the spinal column must be dispersed throughout the affected spinal segments or regions. Nothing in the prior art satisfies these requirements, either individually or in combination.

SUMMARY OF THE DISCLOSURE

In view of the foregoing, it is an object of the present invention to provide an improved system of spinal instrumentation for use in ameliorating aberrant spinal column deviation conditions, such as scoliosis.

It is another object of the present invention to provide an improved method for ameliorating aberrant spinal column deviation conditions, such as scoliosis. It is another object of the present invention to provide an improved system of spinal instrumentation, and a method for the use thereof, for ameliorating aberrant spinal column deviation conditions, such as scoliosis, which system and method facilitates the application of significant derotational forces to individual vertebra, with substantially reduced risk for fracture thereof upon application of such forces.

It is another object of the present invention to provide an improved system of spinal instrumentation, and associated method for use thereof, in ameliorating aberrant spinal column deviation conditions, such as scoliosis, which system and method facilitates the application of forces to vertebrae of affected spinal column segments en bloc, thereby distributing otherwise potentially injurious forces in a manner for safely achieving over-all spinal column correction or derotation.

Applicant's present invention provides a system and method for use of such system which satisfy each of these objectives. Applicant's system includes bone screws which are to be implanted in the pedicle region(s) of individual to-be-derotated vertebrae. In the preferred mode of the present invention, such bone screws are also to be implanted in vertebrae to which balancing forces must be applied as the spinal column is manipulated en mass to achieve an over-all correction of the condition. The pedicle implantation provides a stable foundation for the application of significant derotational forces, but without undue risk of vertebral fracture.

The system includes a pedicle screw cluster derotation tool. This tool, in the presently preferred embodiment includes shafts or similar pedicle screw engagement members, extending from a common handle or linked handle array, which are oriented and configured to extend to and engage the heads of a number of implanted pedicle screws which will have been implanted in adjacent vertebrae to which derotational or balancing forces are to be applied during a spinal column derotation and alignment. The engagement between the pedicle screw cluster derotation tool and the individual pedicle screws is such that, as manipulative forces are applied to the handle means of pedicle screw cluster derotation tool, forces are transferred and dispersed simultaneously among the engaged vertebrae. Therefore, a practitioner may, in a single motion, simultaneously and safely derotate multiple vertebrae of an affected spinal segment (as well as likewise apply balancing forces to other group(s) of vertebrae which are lateral to the effected segment(s).

The effect of practice of the present invention is three-dimensional correction which provides, not only spinal correction to near normal configuration, but corrects "rib humps."

The system of the present invention also includes, in its preferred embodiment, pedicle screws which allow for interfacing with, and fixation relative to pre-contoured spinal rods after a satisfactory derotation.

The present inventor's approach to the problems described above is certainly simple, when viewed in hindsight, but it is equally unobvious. In investigative procedures, the presently proposed system and method has achieved measure of correction of scoliotic curvature never before seen in orthopedic practice.

BRIEF DESCRIPTION OF THE DRAWINGS

The present invention may be more easily understood with reference to figures, which are as follow.

DETAILED DESCRIPTION

With reference to FIGS. 1-4 and 7, the spinal deviation correction system of the present invention includes a number of pedicle screws 10, each implanted in respective vertebrae to which rotative forces will be applied in a spinal anomaly correction.

Pedicle screws 10 may be of a variety of designs, such as, for example, are generally depicted in U.S. Pat. No. 6,743,237 (Gray, et al), U.S. Pat. No. 6,827,719 (Ralph, et al), U.S. Pat. No. 6,652,526 (Arafiles), U.S. Pat. No. 6,375,657 (Doubler, et al), the disclosures of which are incorporated herein by reference.

Figure 3:
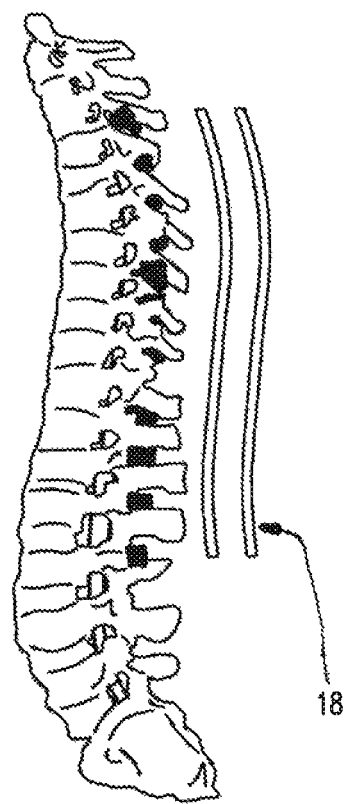
FIG. 3 is an elevational side view of the anatomical model of a human spinal column depicted in FIGS. 1 and 2, with an unobstructed view of already-implanted pedicle screws and adjacent, pre-contoured spinal rods which will be engaged with the pedicle screws through practice of the proposed method.
Figure 4:
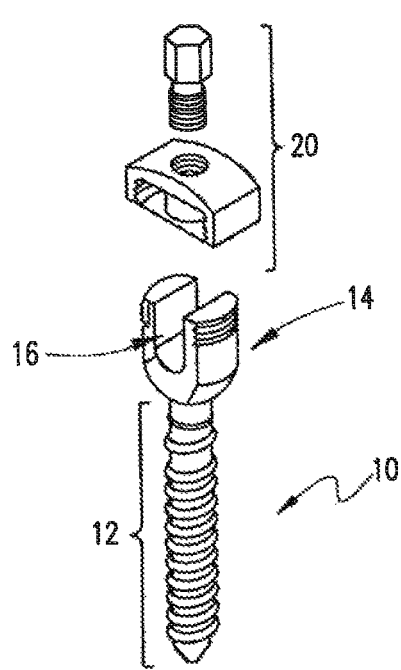
FIG. 4 is an example of a pedicle screw which may be used in the system of the present invention.

With particular reference to FIG. 4, pedicle screws 10 will include a threaded shank segment 12 and a head segment 14. Head segment will be configured with a spinal rod conduit (or channel) 16 or interfacing with a spinal rod 18 (shown in FIG. 3). Spinal rod engagement means 20 serve to fix pedicle screw 10 and spinal rod 18 in relative position and orientation, once a spinal column derotation is complete.

Figure 1:
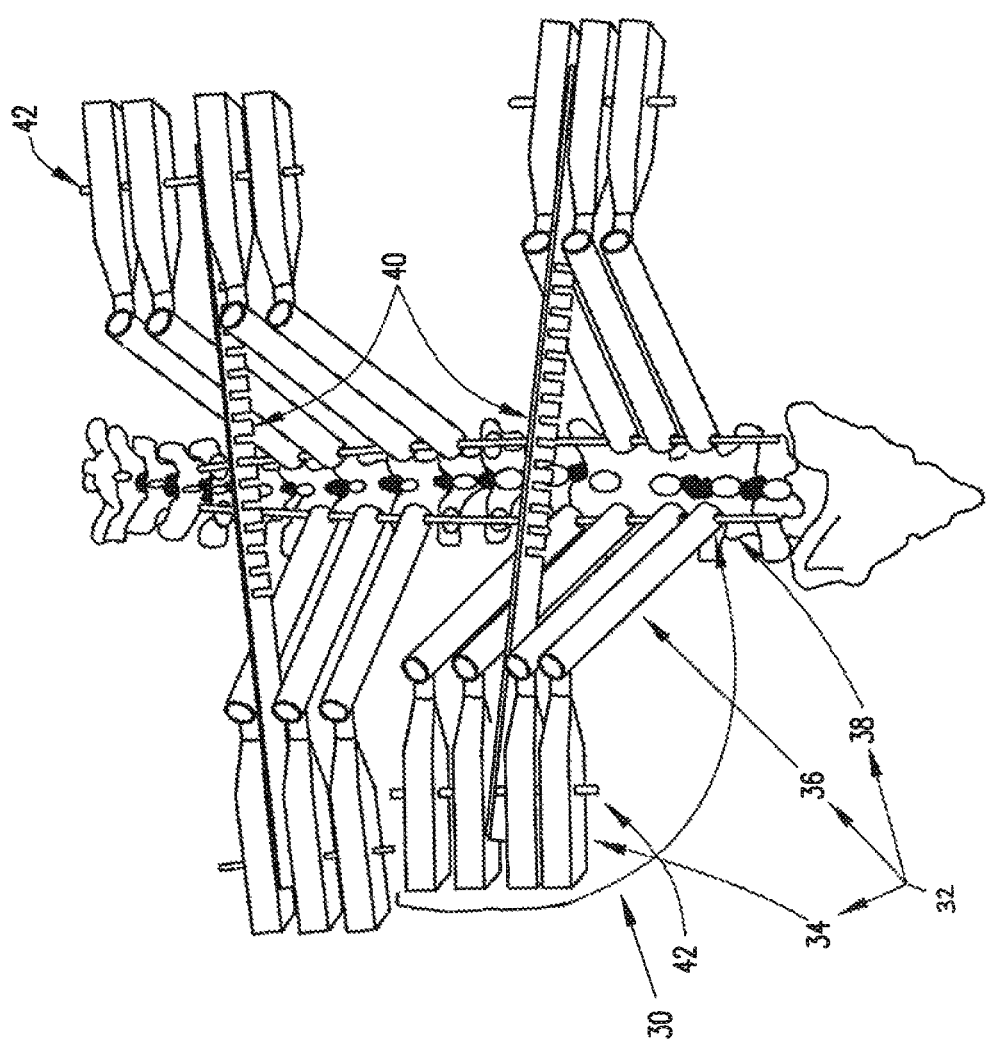
FIG. 1 is a top plan view of an anatomical model of a human spinal column, with components of the system of the present invention shown engaged therewith. The event depicted is that stage of the proposed method after which derotational and balancing forces have been applied to substantially correct a scoliotic curvature.
Figure 2:
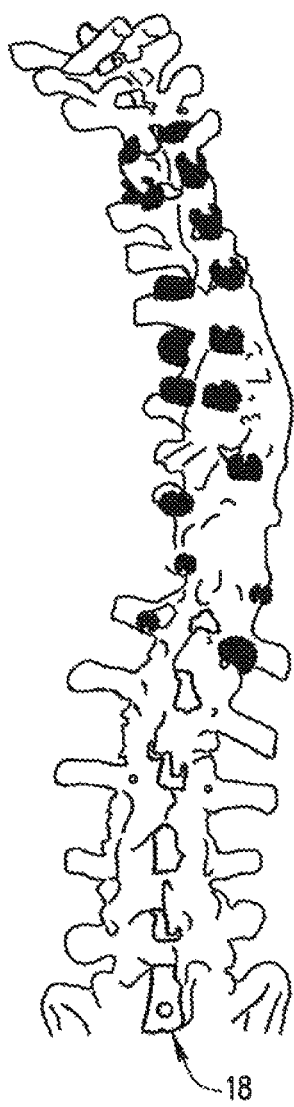
FIG. 2 is an elevational dorsal view of the anatomical model of a human spinal column depicted in FIG. 1, but with an unobstructed view of already-implanted pedicle screws, and configured as if preceding the derotation step of the proposed method.

Referring again, generally to FIGS. 1-4, and 7, the system of the present invention further includes a pedicle screw cluster derotation tool 30. As depicted in FIG. 1, each pedicle screw cluster derotation tool 30 is configured from a grouping of pedicle screw wrenches 32, by a pedicle screw wrench linking member 42 joined together to act in unison during use.

Each pedicle screw wrench 32 includes a handle 34, a shaft 36, and a distal end 38 which is configured to reversibly engage the head segment 14 of a pedicle screw 10 such that, as shaft 36 is moved while shaft distal end 38 is engaged with head segment 14, manipulative forces are transferred to the pedicle screw 10 and, in turn, to the vertebra in which such pedicle screw 10 is implanted.

Significant variations of pedicle screw cluster derotation tool 30 are contemplated by the present invention. For example, the multiple wrenches 32, linked by wrench cross linking members 40, depicted in FIG. 1 may be replaced by a single handle member from which extend the functional equivalent of the multiple shafts 36 and shaft distal ends 38 for simultaneously engaging multiple pedicle screws 10, as depicted. However configured, the object and design of pedicle screw cluster derotation tool 30 is to facilitate simultaneous application of manipulative forces to multiple pedicle screws 10 which are implanted in a like number of vertebra. This has the effect of permitting the gross, en bloc application of sufficient derotative forces to affected segments of the spinal column in a sufficiently dispersed manner as to avoid injury to any one vertebra or isolated spinal column segment. This, in turn, facilitates a successful entire-spine, 3D derotation of a scoliosis patient to near normal parameters.

Figure 5:
FIG. 5 is a depiction of the complimentary forces applied to multiple spinal column segments to achieve an over-all spinal column correction.
Figure 7:
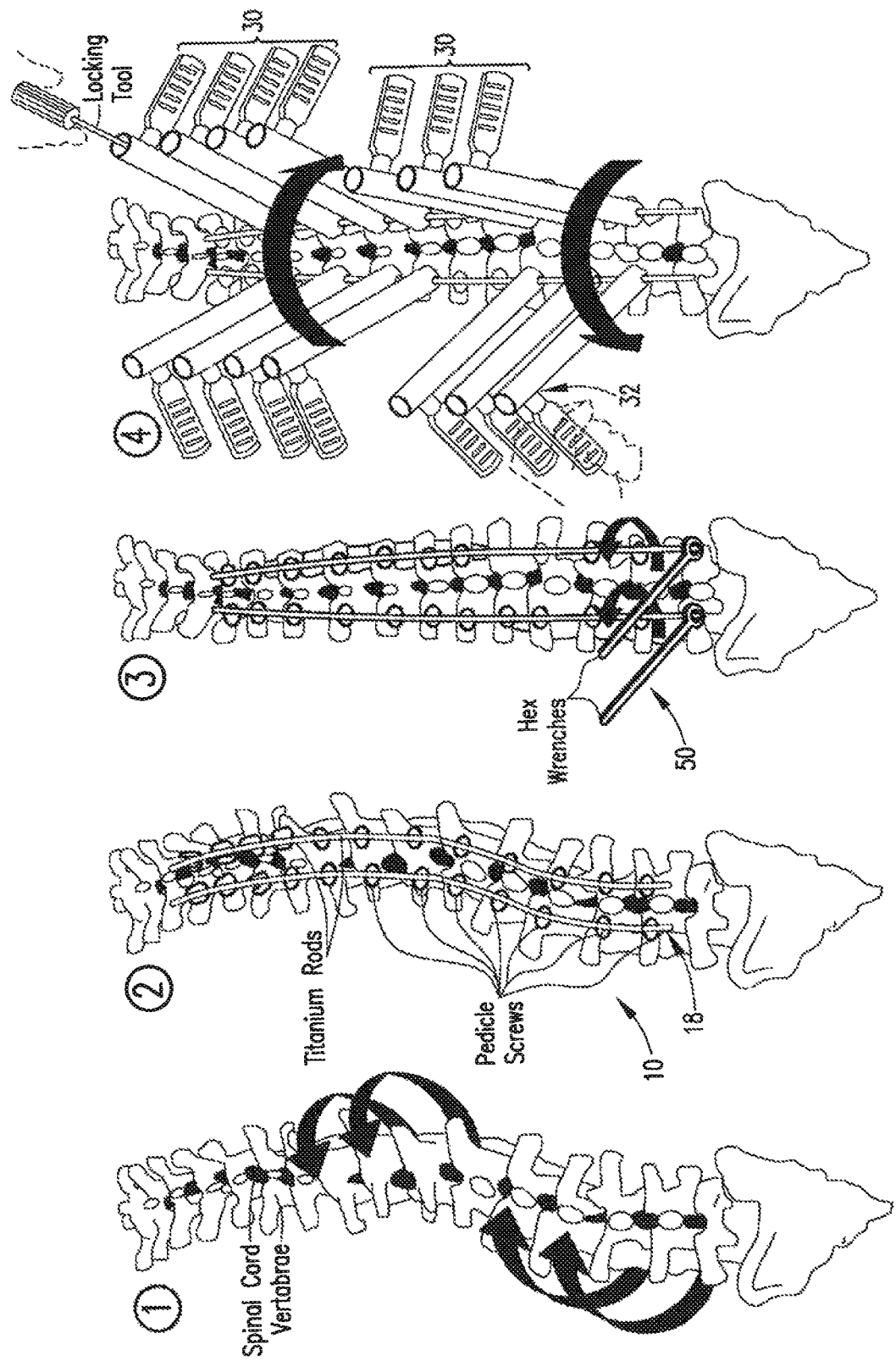
FIG. 7 is a 4-frame, progressive animation of the stages of correction of scoliosis according to the embodiments of the present invention.

With reference to FIGS. 1-3, 5 and 7 the preferred mode of the present method usually involves application of forces to multiple spinal column segments, to achieve an over-all spinal column correction. For example, as depicted in FIGS. 5 and 7 in the case of a single curvature case of scoliosis, both derotative forces (illustrated by the central force vector arrow of FIG. 5) to vertebrae involved in scoliotic curvatures, as well as of balancing, or offsetting forces to lateral spinal segments (illustrated by the lateral arrows of FIG. 5) are applied.

The preferred mode of the present method involves pre-contouring spinal rods member 18, as shown in FIG. 3 and frame 2 of FIG. 7. Such a contouring operation involves bending spinal rods member 18 such that, in along two axes (analogous to yaw and pitch in aviation terms), the spinal rods member 18 will substantially define, in one plane, a desired post-operative correction of the affected spinal column in reference to such two axes.

The spinal rod(s) member 18 are loosely engaged with pedicle screws 10, and in one of the embodiments of the present invention the pre-contoured spinal rod member 18 are rotated from a first orientation, through approximately 90 degree to a second orientation, using hex wrenches 50 (see frame 3 of FIG. 7), to achieve a substantial correction of the scoliosis in the first two of three axes which will be corrected according to one of the embodiments of the present methodology, through use of the present system.

The next phase, after 2-D correction as just described, involves applying manipulative forces to pedicle screw clusters in reference to a third axis (a "roll axis", again using aviation terms) using pedicle screw clusters derotation tool(s) 30 (see, inter alia, frame 4 of FIG. 7). After this final correction, spinal rod engagement member 20 is tightened to fix pedicle screw 10 and spinal rod 18 in relative position and orientation to secure the corrected spinal column configuration (now corrected with reference to all three relevant axes).

Spinal rod engagement member 20 of pedicle screws 10 are tightened, using an anti-torque feature of wrenches 32 (or of their equivalent in an alternative embodiment). This feature, as is well known in the art, allows tightening of nuts and the like, without imparting undue torque to the underlying apparatus or structure.

Figure 6:
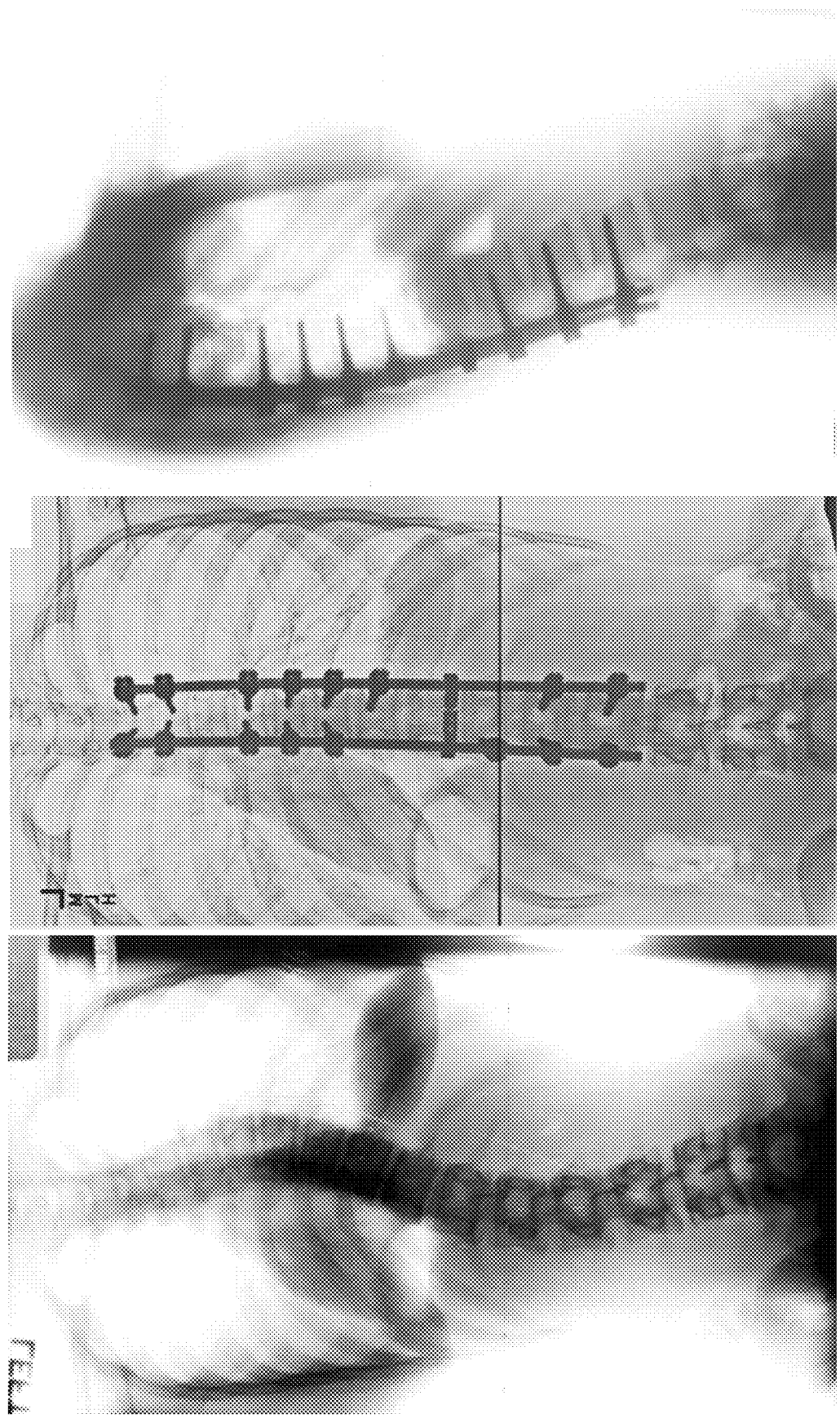
FIG. 6 is a three frame x-ray view showing "before and after" views of a scoliosis patient who was treated in an investigational procedure in the development of the systems and methods of the present disclosure. The curvature correction was substantially to normal, and lumbar motion was preserved notwithstanding.

As shown in FIG. 6, investigative practice of at least one of the present methods disclosed herein achieves efficacy never before seen in the orthopedic field. The "before picture" is the left hand image of FIG. 6, and the two remaining images are sagittal and dorsal views of the corrected spinal column.

Although the invention has been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

What is claimed is:

1. A system for applying a manipulative force to a target region of a spinal column during a surgical procedure, the system comprising:
   a first plurality of elongated levers each having a proximal portion and a distal portion, each distal portion being configured to temporarily engage with a proximal portion of a pedicle screw implanted in a vertebra, the first plurality of elongated levers being interconnected to form a first linked handle array; and
   a second plurality of elongated levers each having a proximal portion and a distal portion, each distal portion being configured to temporarily engage with a proximal portion of a pedicle screw implanted in a vertebra, the second plurality of elongated levers being interconnected to form a second linked handle array, wherein the system permits an operator to apply a derotation force in a first direction through the first linked handle array to a first set of vertebrae during a surgical procedure, and permits the operator to simultaneously apply a balancing force in a second direction opposite to the first direction through the second linked handle array to a second set of vertebrae, and wherein the first plurality of elongated levers and the second plurality of elongated levers are surgical instruments and are not part of a construct configured to be implanted in, on or remain attached to a patient, but rather are configured to be temporarily engaged with the pedicle screws during the surgical procedure, used to apply forces to the pedicle screws during the same surgical procedure, and removed from the pedicle screws and the patient during the same surgical procedure.

2. The system of claim 1, further comprising a plurality of pedicle screws each having a channel located on its proximal portion configured to receive a spinal rod.

3. The system of claim 2, further comprising:
a spinal rod configured to extend in an axial direction between a first pedicle screw and a second pedicle screw of the plurality of pedicle screws;
a spinal rod engagement mechanism provided on the proximal portions of each of the first and second pedicle screws configured to secure the spinal rod to the proximal portions of the first and second pedicle screws.

4. The system of claim 1, wherein the first linked handle array is configured to allow the first plurality of elongated levers to temporarily engage with two pedicle screws implanted in a single vertebra.

5. The system of claim 1, wherein each of the elongated levers of the first and second linked handle arrays are configured to initially extend away from the proximal portion of their respective pedicle screws along a longitudinal axis of the respective pedicle screw.

6. The system of claim 1, wherein the first linked handle array comprises a single handle member configured to receive the derotation force.

7. The system of claim 1, wherein the second linked handle array comprises a single handle member configured to receive the balancing force.

8. The system of claim 1, further comprising a third plurality of elongated levers each having a proximal portion and a distal portion, each distal portion being configured to temporarily engage with a proximal portion of a pedicle screw implanted in a vertebra, the third plurality of elongated levers being interconnected to form a third linked handle array, wherein the system permits an operator to apply a derotation force or a balancing force through the third linked handle array to a third set of vertebrae.

9. The system of claim 1, wherein the first plurality of elongated levers extend at least partially in a dorsal direction when temporarily engaged with the pedicle screws implanted in the vertebrae.

10. The system of claim 1, wherein each of the first plurality of elongated levers and each of the second plurality of elongated levers is configured such that the distal portion of the elongated lever resides inside a patient's body engaged with the proximal portion of an associated pedicle screw when the elongated lever is in use, and the proximal portion of the elongated lever resides outside the patient's body when in use.

11. The system of claim 1, wherein the elongated levers comprise a generally cylindrical shape.

12. The system of claim 1, wherein the elongated levers comprise a transverse cross-section that is circular in shape.

13. The system of claim 1, wherein the elongated levers are configured to engage a head portion of an associated pedicle screw, the head portion having a larger diameter than a shank portion of the associated pedicle screw.

14. The system of claim 1, wherein the elongated levers are configured to engage a proximal-most portion of an associated pedicle screw.

15. A surgical kit comprising:
a first plurality of elongated levers each having a proximal portion and a distal portion, each distal portion being configured to temporarily engage with a proximal portion of a pedicle screw implanted in a vertebra, the first plurality of elongated levers configured to be interconnected to form a first linked elongated lever array; and
a second plurality of elongated levers each having a proximal portion and a distal portion, each distal portion being configured to temporarily engage with a proximal portion of a pedicle screw implanted in a vertebra, the second plurality of elongated levers configured to be interconnected to form a second linked elongated lever array,
wherein the surgical kit, once assembled and in use, permits an operator to apply a derotation force in a first direction through the first linked elongated lever array to a first set of vertebrae during a surgical procedure, and permits the operator to simultaneously apply a balancing force in a second direction opposite to the first direction through the second linked elongated lever array to a second set of vertebrae, and
wherein the first plurality of elongated levers and the second plurality of elongated levers are surgical instruments and are not part of a construct configured to be implanted in, on or remain attached to a patient, but rather are configured to be temporarily engaged with the pedicle screws during the surgical procedure, used to apply forces to the pedicle screws during the same surgical procedure, and removed from the pedicle screws and the patient during the same surgical procedure.

16. The surgical kit of claim 15, further comprising a plurality of pedicle screws each having a channel located on its proximal portion configured to receive a spinal rod.

17. The surgical kit of claim 16, further comprising:
a spinal rod configured to extend in an axial direction between a first pedicle screw and a second pedicle screw of the plurality of pedicle screws; and
a spinal rod engagement mechanism provided on the proximal portions of each of the first and second pedicle screws configured to secure the spinal rod to the proximal portions of the first and second pedicle screws.

18. The surgical kit of claim 15, wherein the first linked elongated lever array is configured to allow the first plurality of elongated levers to temporarily engage with two pedicle screws implanted in a single vertebra.

19. The surgical kit of claim 15, wherein each of the elongated levers of the first and second linked elongated lever arrays are configured to initially extend away from the proximal portion of their respective pedicle screws along a longitudinal axis of the respective pedicle screw.

20. The surgical kit of claim 15, further comprising a handle member configured to be coupled with the first linked elongated lever array and to receive the derotation force.

21. The surgical kit of claim 15, further comprising a handle member configured to be coupled with the second linked elongated lever array and to receive the balancing force.

22. The surgical kit of claim 15, further comprising a third plurality of elongated levers each having a proximal portion and a distal portion, each distal portion being configured to temporarily engage with a proximal portion of a pedicle screw implanted in a vertebra, the third plurality of elongated levers configured to be interconnected to form a third linked elongated lever array, wherein the surgical kit permits an operator to apply a derotation force or a balancing force through the third linked elongated lever array to a third set of vertebrae.

23. The surgical kit of claim 15, further comprising a linking member configured to interconnect at least some of the first or second plurality of elongated levers in an axial direction such that they can be moved together in unison.

24. The surgical kit of claim 15, further comprising a cross-linking member configured to interconnect at least some of the first or second plurality of elongated levers in a transverse direction such that they can be moved together in unison.

25. The surgical kit of claim 15, wherein the first plurality of elongated levers extend at least partially in a dorsal direction when temporarily engaged with the pedicle screws implanted in the vertebrae.

26. The surgical kit of claim 15, wherein each of the first plurality of elongated levers and each of the second plurality of elongated levers is configured such that the distal portion of the elongated lever resides inside a patient's body engaged with the proximal portion of an associated pedicle screw when the elongated lever is in use, and the proximal portion of the elongated lever resides outside the patient's body when in use.

27. The surgical kit of claim 15, wherein the elongated levers comprise a generally cylindrical shape.

28. The surgical kit of claim 15, wherein the elongated levers comprise a transverse cross-section that is circular in shape.

29. The surgical kit of claim 15, wherein the elongated levers are configured to engage a head portion of an associated pedicle screw, the head portion having a larger diameter than a shank portion of the associated pedicle screw.

30. The surgical kit of claim 15, wherein the elongated levers are configured to engage a proximal-most portion of an associated pedicle screw.

* * * * *